(12) United States Patent
Uchida et al.

(10) Patent No.: US 9,427,379 B2
(45) Date of Patent: Aug. 30, 2016

(54) DENTAL MATERIAL SET AND A DENTAL MEMBRANE FOR OBSCURING A METAL COLOR OF A DENTAL METAL, AND A PREPARING METHOD THEREOF

(71) Applicant: KABUSHIKI KAISHA SHOFU, Kyoto (JP)

(72) Inventors: Jun Uchida, Kyoto (JP); Mitsuji Teramae, Kyoto (JP); Shuhei Takahashi, Kyoto (JP); Masanori Goto, Kyoto (JP); Ryuichi Yoshimoto, Kyoto (JP)

(73) Assignee: KABUSHIKI KAISHA SHOFU, Kyoto (JP)

( * ) Notice: Subject to any disclaimer, the term of this patent is extended or adjusted under 35 U.S.C. 154(b) by 155 days.

(21) Appl. No.: 14/223,154

(22) Filed: Mar. 24, 2014

(65) Prior Publication Data
US 2014/0295376 A1    Oct. 2, 2014

(30) Foreign Application Priority Data
Mar. 26, 2013    (JP) .................... 2013-064520

(51) Int. Cl.
*A61K 6/08* (2006.01)
*A61K 6/00* (2006.01)
*A61C 13/08* (2006.01)

(52) U.S. Cl.
CPC ............ *A61K 6/0023* (2013.01); *A61C 13/082* (2013.01); *A61K 6/0005* (2013.01); *A61K 6/0008* (2013.01)

(58) Field of Classification Search
CPC .................................................. A61K 6/0008
See application file for complete search history.

(56) References Cited

U.S. PATENT DOCUMENTS

2010/0081728 A1* 4/2010 Uchida ............... A61K 6/0094
523/105
2011/0065828 A1   3/2011 Okubayashi et al.

FOREIGN PATENT DOCUMENTS

DE   10 2007 055 056   5/2009
JP        10-273305   10/1998
(Continued)

OTHER PUBLICATIONS

Takashi Miyazaki et al., Clinical Dental Materials, May 2006, 1st Edition, edited Apr. 20, 2012, with partial English language translation thereof.
(Continued)

*Primary Examiner* — Michael Pepitone
(74) *Attorney, Agent, or Firm* — Wenderoth, Lind & Ponack, L.L.P.

(57) ABSTRACT

Provided are opaque materials exhibiting a good adhesive strength and a good color tone reproduction comparable with natural dental crowns as well as having a good operability. In addition, the opaque materials may exhibit a stain-resistance property in rebuilding-up a dental composition on the opaque materials in a cured form with a metal instrument. Further, the opaque materials may exhibit a good color tone reproduction comparable with natural dental crowns even if a dental membrane is thinly formed from the opaque metals. The dental membrane is formed from a first opaque layer and a second opaque layer, wherein the first opaque layer contains a filler of indefinite-shape particles and the second opaque layer contains a filler of spherical-shape particles, and wherein the first opaque layer is formed on a metal base and the second opaque layer is formed on the first opaque layer.

8 Claims, 2 Drawing Sheets

(56) References Cited

FOREIGN PATENT DOCUMENTS

| JP | 11-92461 | 4/1999 |
| JP | 2000-198966 | 7/2000 |
| JP | 2002-226316 | 8/2002 |
| JP | 2003-238326 | 8/2003 |
| JP | 2006-52128 | 2/2006 |
| JP | 2008-94732 | 4/2008 |
| JP | 2010-215694 | 9/2010 |
| JP | 2012-87086 | 5/2012 |

OTHER PUBLICATIONS

Extended European Search Report issued Dec. 12, 2014 in corresponding European Application No. 14161421.4.

* cited by examiner

DENTAL MATERIAL SET AND A DENTAL MEMBRANE FOR OBSCURING A METAL COLOR OF A DENTAL METAL, AND A PREPARING METHOD THEREOF

FIELD OF THE INVENTION

The present invention relates to a novel dental material set for obscuring a metal color of a dental metal and a use thereof. Particularly, the present invention relates to a dental material set for obscuring a metal color of a dental metal which exhibits a good color tone reproduction, a good adhesiveness to dental metals, and a good impact resistance and the use thereof. Further, the dental material set has a good operability and a good curing property. The present invention also relates to a dental membrane for obscuring a metal color of a dental metal, the dental membrane formed from opaque materials comprised in the dental material set according to the present application.

BACKGROUND

An aesthetic view is one of important matters in current dental treatments. Dental materials are strongly desired to have adequate color tone comparable with natural teeth or exhibit a beautiful color of white.

To meet the needs of the aesthetic view, instead of dental metals ceramics or resin materials are used as a dental restorative material. In such a way, a natural dental crown color is reproduced. Particularly, resin materials have been extensively developed. In recent years, some of resin materials have a sufficient abrasion resistance, bending strength, and water resistance.

Particularly, the resin materials are very often used to form facing crowns. Facing crowns are a crown restoration that is a sort of dental veneers. The outer part of the facing crowns is formed from a teeth crown material such as resin materials. As a result, the facing crowns provide not only adequate functions in the oral cavity but also adequate aesthetic. A preparation procedure is illustrated below.

First, an appropriate pre-treatment such as sandblasting is applied to a metal cast called a metal frame and then, a primer for bonding metal is applied to the treatment surface with a brush.

Retention beads may be attached to the surface of the metal frame in order to obtain an irregular surface which yields an increased mechanical bond to a resin material. A preopaque material may be applied and cured on the surface to which retention beads are applied in order to fill several voids between retention beads and to enhance the adhesion strength. Subsequently, to conceal the metal color of the metal frame, an opaque material is applied and cured which consists of a hardening composition and has a high contrast ratio. The procedure of applying and curing such hardening composition in the paste form is repeated as required. After an adequate concealment of the metal color is obtained, a hardening resin paste for forming dental crown is gradually rebuilt-up and cured on the cured form of the resin. The process is, as required, repeated to finally make a teeth form (non-patent literature 1).

If the adhesive strength is not adequate between the metal frame and the opaque material, the cured form of the opaque material or hardening resin paste is peeled off from the surface of the metal. As a result, remaking of a teeth form is required. Alternatively, a dye caused from food and drink gets into an interspace between the metal frame and the cured form of the opaque material and the aesthetic view becomes inadequate.

Several primers for bonding metal having high properties have been developed (patent literatures 1, 2, and 3). However, there are still problems including chippage of cured resins, peel-off from metal frames, and inadequate appearance due to stains which may be caused from a poor adhesive strength between cured resins and metal frames. It is thought that these problems may be caused in part from inadequate adherence properties between primers for bonding metal and opaque materials.

In addition, a good operability in use is an important factor for opaque materials when in the paste form. If opaque materials have inadequate operability, it is difficult to uniformly apply the opaque material, possibly resulting in a poor adhesive strength and inadequate aesthetic view. If the opaque materials exhibit an adhesive property, surface hardness, mechanical strength, and aesthetic view become inadequate.

Several different opaque materials and opaque sets as opaque composition have been developed (patent literatures 4, 5, 6, and 7). However, opaque compositions comprising one type of opaque material have a tendency to decrease in adhesive strength as compared to opaque compositions comprising two or three types of opaque materials. In view of operability, such one-type opaque compositions do not fully fill voids between several retention beads which are attached to a surface of dental materials. Further, one-type compositions easily droop because of a low viscosity in the paste form, which is inadequate as an obscure material. Such inadequate property may be improved by combining two or three type of opaque materials. There are still problems regarding operability in the paste form, color tone reproduction, and mechanical strength.

Moreover, a hard resin is applied and polymelized to make an upper construction. In the procedure, a metal instrument generally used to make the upper construction. The metal instrument is shaved at edges of filler particles comprised in the hardened opaque materials and the surface of the hardened opaque materials is stained with black color, resulting in a poor aesthetic view.

An important problem to be solved is to provide an opaque material set that exhibits a good durable adhesiveness, adhesive strength and good color tone reproduction comparable with natural dental crowns as well as have a good operability. In late years, a hard resin has a good color tone reproduction in that the hardened materials exhibit white color similar or superior to natural dental crowns. It is important for opaque materials to have a good property so that metal colors of metal frames are concealed. Opaque materials are expected to adequately conceal metal colors and to reproduce color tone and transparency of upper constructions. Accordingly, there are needs for an opaque material set or composition to fill voids between several retention beads and exhibit a good mechanical strength, have an adequate concealment of color, reproduce a color tone comparable with natural dental crowns, and a reproducible operability so that an opaque material is thinly applied.

RELATED PRIOR ART

Non-Patent Literature 1

Takashi Miyazaki, Hiroshi Nakajima, Tatsushi Kawai, & Yutaka Oda. (May 2006). *Clinical Dental Materials, Ishiyaku Publishers, Inc.*

[Patent literature 1] JP H11-092461 A
[Patent literature 2] JP 2000-198966 A
[Patent literature 3] JP 2003-238326 A
[Patent literature 4] JP 2002-226316 A
[Patent literature 5] JP 2006-52128 A
[Patent literature 6] JP 2008-94732 A
[Patent literature 7] JP 2010-215694 A

SUMMARY OF THE INVENTION

Problem to be Solved by the Invention

An object of the invention is to provide an opaque material which not only exhibits a good adhesive strength and a good color tone reproduction comparable with natural dental crowns but also has a good operability. In addition, the opaque material exhibits a stain-resistance property in rebuilding-up a dental composition on the opaque materials in the cured form with a metal instrument. Further, the opaque material exhibits a good color tone reproduction comparable with natural dental crowns even if a dental membrane is thinly formed from the opaque materials.

Means to Solve the Problem

The inventors keenly investigated several materials and arrived at the present invention. In particular, the inventors discovered that a dental material set for obscuring a metal color comprising a first opaque material (A) and a second opaque material (B) is used to form a dental membrane including a first opaque layer and a second opaque layer and thus, the above problem is solved. The first opaque material (A) contains a polymerizable monomer (a1) in an amount of 100 parts by weight; an inorganic filler (a2) of indefinite-shape particles whose average particle size ranges from 0.1 µm to 20 µm in an amount ranging from 10 to 150 parts by weight; a polymerization catalyst (a3) in an amount ranging from 0.1 to 10 parts by weight; and an obscure material (a4) in an amount ranging from 0.5 to 20 parts by weight. The second opaque material (B) contains a polymerizable monomer (b1) in an amount of 100 parts by weight; an inorganic filler (b2) of spherical-shape particles whose average particle size ranges from 0.1 µm to 0.20 µm in an amount ranging from 10 to 200 parts by weight; a polymerization catalyst (b3) in an amount ranging from 0.5 to 20 parts by weight; and an obscure material (b4) in an amount ranging from 1 to 25 parts by weight. The present invention is based the discovery that the above problem is solved by applying the first opaque material to a surface of a metal frame and curing the first opaque material to form a cured resin (a first opaque layer), and applying the second opaque material on the first opaque layer and curing to form a cured resin (a second opaque layer).

With reference to a dental material set for obscuring a metal color according to the present invention, the step of forming a multi-layer construction which contains the first opaque layer formed on a metal frame and the second opaque layer formed on the first opaque layer is described.

Figure 1:
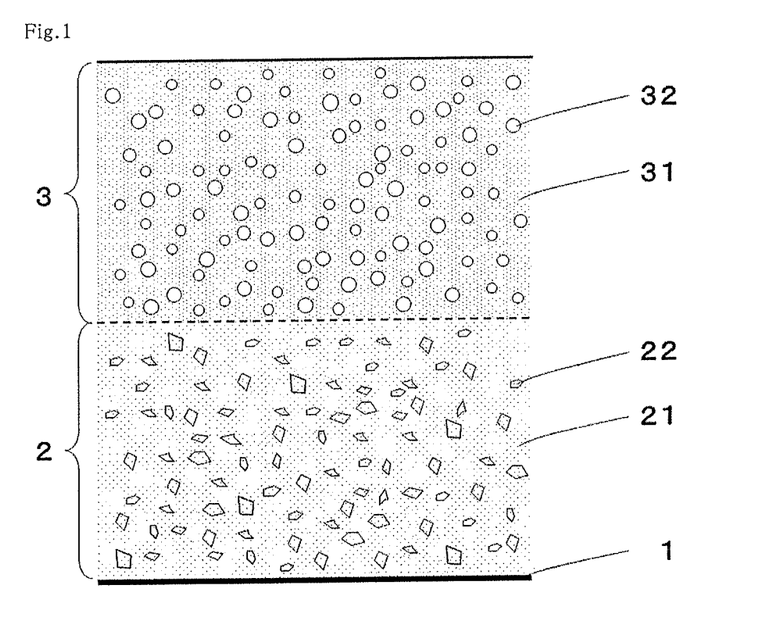
FIG. 1 shows a schematic of a cross-section of a dental membrane for obscuring a metal color which is formed on a surface of a dental metal, according to the first embodiment.

A first embodiment of the present invention is illustrated in FIG. 1. In the embodiment, a first opaque material (A) is applied to a metal surface 1 of a metal frame and is cured by photo-polymerization and/or thermo-polymerization to form a first opaque layer 2. In the present invention, the first opaque layer 2 contains an inorganic filler 22 of indefinite-shape particles whose average particle size ranges from 0.1 µm to 20 µm. The inorganic filler 22 is dispersed in the cured form 21 of a resin (polymerizable monomer) which constitutes the first opaque layer 2. Then, a second opaque material (B) is applied to the first opaque layer 2 at least one or more and is cured by photo-polymerization and/or thermo-polymerization to form a second opaque layer 3. In the present invention, the second opaque layer 3 contains an inorganic filler 32 of spherical-shape particles whose average particle size ranges from 0.1 µm to 20 µm. The inorganic filler 32 is dispersed in the cured form 31 of a resin (polymerizable monomer). To exhibit an obscure effect, the first opaque layer 2 and the second opaque layer 3 contain obscure materials 23 and 33, respectively, which are not shown in FIG. 1.

Figure 2:
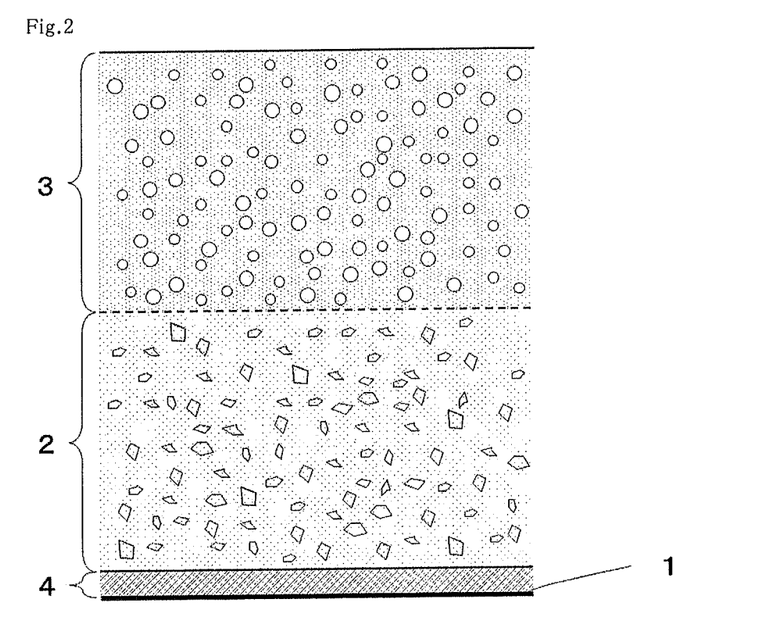
FIG. 2 shows a schematic of a cross-section of a dental membrane for obscuring a metal color which is formed on a surface of a dental metal, according to the second embodiment.

A second embodiment of the present invention is illustrated in FIG. 2. In this embodiment, a metal surface treatment agent for adhesion (C) is applied to the metal surface and dried to form a surface treatment film 4 in order to improve adhesiveness between a surface 1 of a dental metal and the first opaque layer 2.

Figure 3:
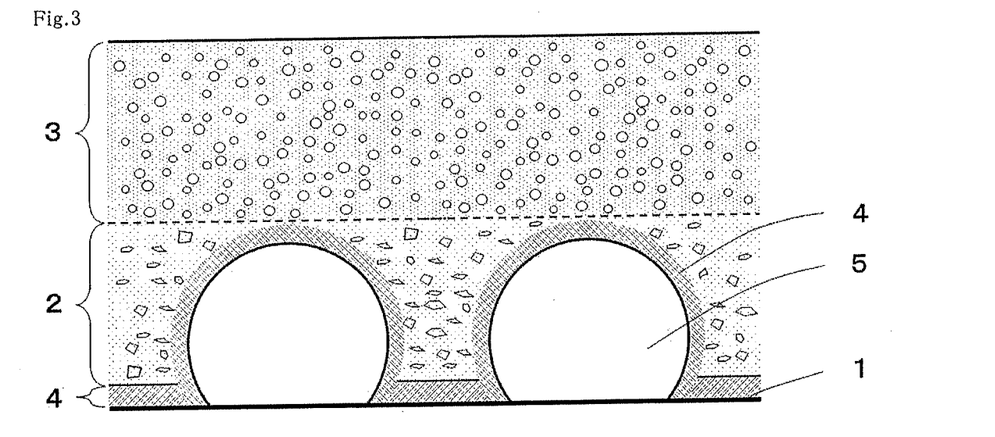
FIG. 3 shows a schematic of a cross-section of a dental membrane for obscuring a metal color which is formed on a surface of a dental metal to which retention beads are applied, according to the third embodiment.

A third embodiment of the present invention is illustrated in FIG. 3. In this embodiment, retention beads 5 is applied to a surface 1 of a dental metal for providing an anchoring effect, which may prevent an opaque layer from being peeled off from the metal surface. Similar to the first and second embodiments, the first opaque layer 2 and the second opaque layer 3 and/or the surface treatment film 4 may be formed after applying the retention beads 5 to the metal surface.

The present invention provides an opaque material which not only exhibits a good adhesive strength and a good color tone reproduction comparable with natural dental crowns but also has a good operability. In addition, the opaque material exhibits a stain-resistance property in rebuilding-up a dental composition on the opaque material in the cured form with a metal instrument. Further, the opaque material exhibits a good color tone reproduction comparable with natural dental crowns even if a dental membrane is thinly formed from the opaque metals.

DETAILED DESCRIPTION OF THE INVENTION

[Polymerizable Monomer]

Polymerizable monomers known in the art are used, without any limitation, for a polymerizable monomer (a1) and a polymerizable monomer (b1) according to the invention.

In the present invention, the polymerizable monomers may be monofunctional compounds including (meth)acrylic ester such as methyl(meth)acrylate, ethyl(meth)acrylate, n-butyl(meth)acrylate, isobutyl(meth)acrylate, tert-butyl (meth)acrylate, pentyl(meth)acrylate, isopentyl(meth)acrylate, neopentyl(meth)acrylate, glycidy(meth)acrylate, tetrahydrofurfuryl(meth)acrylate, 2-hydroxyethyl(meth)acrylate, 2-hydroxypropyl(meth)acrylate, 3-chloro-2-hydroxypropyl (meth)acrylate, ethylene glycolacetate(meth)acrylate, ethylene glycolmono(meth)acrylate, diethylene glycolmono(meth)acrylate, triethylene glycolmono(meth)acrylate, polyethylene glycolmono(meth)acrylate, methoxydiethylene glycolmono(meth)acrylate, methoxy tetraethylene glycol(meth)acrylate, methoxy polyethylene glycol(meth)acrylate, beta-(meth)acryloxyethyl hydrogen phthalate, beta-(meth)acryloxyethyl hydrogen succinate, nonylphenoxyethyl(meth)acrylate, phenoxyethyl(meth) acrylate, phenoxydiethylene(meth)acrylate, N-(2-hydroxy-3-(meth)acryloyloxypropyl)-N-phenylglycine, N-(meth) acryloylglycine, 4-(meth)acryloyloxyethyl trimellitic anhydride; vinylester such as vinyl acetate and vinyl propionate; vinylether such as methyl vinylether, ethyl vinylether, isobutyl vinylether and (meth)acrylaldehyde ethylacetal; alkenylbenzene such as styrene, vinyltoluene, α-methylstyrene, chlorostyrene; vinyl cyanide such as acrylonitrile and (meth)acrylonitrile; (meth)acrylaldehyde such as (meth) acrylaldehyde and 3-cyano(meth)acrylaldehyde; (meth) acrylic acid amide such as (meth)acrylamide, N-succin (meth)acrylamide and N,N-dimethyl(meth)acrylamide; (meth)acrylic acid such as (meth)acrylic acid, vinylacetic acid and crotonic acid, and a metal salt thereof; phosphate ester group-containing polymerizable monomer such as acid phosphoethyl(meth)acrylate, acid phosphopropyl(meth) acrylate and 2-(meth)acryloyloxyethyl phenyl phosphoric acid, and a metal salt thereof; monomer having a sulfonic acid group such as acrylic sulfonic acid, (meth)acrylic sulfonic acid, sthylene sulfonic acid, and tert-butyl(meth) acrylamide sulfonic acid, and a metal salt thereof.

In the present invention, the polymerizable monomers may be bifunctional polymerizable monomers including di(meth)acrylate such as ethylenediol, propylenediol, propanediol, butanediol, hexanediol, octanediol, nonanediol, decanediol, eicosanediol; ethylene glycol di(meth)acrylate, diethylene glycol di(meth)acrylate, triethylene glycol di(meth)acrylate, propylene glycol di(meth)acrylate, tetraethylene glycol di(meth)acrylate, polyethylene glycol di(meth)acrylate, 1,3-butylene glycol di(meth)acrylate, neopentyl glycol di(meth)acrylate; urethane-based polymerizable monomer which is derived from an adduct of a vinyl monomer having a hydroxy group such as 2-hydroxyethyl (meth)acrylate, 2-hydroxypropyl (meth)acrylate and 3-chloro-2-hydroxypropyl (meth)acrylate, and a diisocyanate compound such as hexamethylene diisocyanate, trimethyl hexamethylene diisocyanate, diisocyanate methylcyclohexane, isofluoro diisocyanate and methyl bis(4-cyclohexyl isocyanate); aromatic ring and urethane bond-containing (meth)acrylate-based polymerizable monomer which is derived from an adduct of a vinyl monomer having a hydroxy group such as 2-hydroxyethyl (meth)acrylate, 2-hydroxypropyl (meth)acrylate and 3-chloro-2-hydroxypropyl (meth)acrylate, and an aromatic group-containing diisocyanate compound such as diisocyanate methyl benzene and 4,4'-diphenyl methane diisocyanate; a reactant of 1:2 ratio of (meth)acrylate-based polymerizable monomer which has an aromatic ring and an ether linkage, bisphenol A or hydrogenated bisphenol A such as 2,2-bis((meth)acryloxy phenyl)propane, 2,2-bis(4-(3-(meth)acryloxy-2-hydroxypropoxyphenyl)propane, 2,2-bis (4-(meth)acryloxy ethoxyphenyl)propane, 2,2-bis(4-(meth) acryloxy diethoxyphenyl)propane, 2,2-bis(4-(meth)acryloxy tetraethoxyphenyl)propane, 2,2-bis(4-(meth)acryloxy pentaethoxyphenyl)propane, 2,2-bis(4-(meth)acryloxy polyethoxyphenyl)propane, 2,2-bis(4-(meth)acryloxy dipropooxyphenyl)propane, 2-(4-(meth)acryloxy ethoxyphenyl)-2-(4-(meth)acryloxy phenyl)propane, 2-(4-(meth) acryloxy diethoxyphenyl)-2-(4-(meth)acryloxy triethoxyphenyl)propane, 2-(4-(meth)acryloxy dipropoxyphenyl)-2-(4-(meth)acryloxy triethoxyphenyl)propane and 2,2-bis(4-(meth)acryloxy isopropoxyphenyl)propane to glycyl(meth) acrylate, e.g., a reactant of 1:2 ratio of a bisphenol A or hydrogenated bisphenol A such as a bisphenol A diglycidyl ether(meth)acrylic acid adduct to an epoxy group containing (meth)acrylate.

In the present invention, the polymerizable monomers may be trifunctional polymerizable monomers including trimethylolmethane tri(meth)acrylate, trimethylolethane tri (meth)acrylate, trimethylolpropane tri(meth)acrylate, pentaerythritol tetra(meth)acrylate, phosphazene-based tri (meth)acrylate, isocyanuric acid-based tri(meth)acrylate, pentaerythritol tetra(meth)acrylate, and ditrimethylolpropane tetra(meth)acrylate, or urethane-based polymerizable monomer which is derived from a vinyl monomer having a hydroxy group such as glycidol di(meth)acrylate, and a diisocyanate compound such as diisocyanate methylbenzene, 4,4'-diphenylmethane diisocyanate, hexamethylene diisocyanate, trimethylhexamethylene diisocyanate, diisocyanate methyl cyclohexane, isophorone diisocianate and methyl bis(4-cyclohexylisocyanate), polymerizable monomer having five or more ethylenically unsaturated groups such as dipentaerythritol hydroxypenta(meth)acrylate, polymerizable multifunctional acrylate having polyethylenically unsaturated carbamoylisocianate; urethane bond-containing polymerizable multifunctional acrylate such as phenylglycidyletheracrylate hexamethyllene diisocianate urethane prepolymer, phenylglycidylether toluene diisocyanate urethane prepolymer, pentaerythritol triacrylate toluene diisocyanate urethane prepolymer and pentaerythritol triacrylate isophorone diisocyanate urethane prepolymer; ditrimethylolpropane tetraacrylate, ethoxylated pentaerythritol tetraacrylate, propoxylated pentaerythritol tetraacrylate, pentaerythritol tetra(meth)acrylate, dipentaerythritol tetra (meth)acrylate, dipentaerythritol penta(meth)acrylate, dipentaerythritol hexa(meth)acrylate and trimethyl propane tri(meth)acrylate.

These polymerizable monomers may be used alone or in combination of two or more thereof. In the present invention, instead of using polymerizable monomers, polymerizable oligomers consisting of some polymerizable monomers may be used.

[Inorganic Filler]
<Composition>

In the present invention, inorganic fillers known as dental material may be used for the inorganic filler (a2) and the inorganic filler (b2). Examples of the inorganic filler include, but are not limited to, soda-lime glass, lithium borosilicate glass, barium glass, strontium glass, zinc glass, fluoro-aluminum borosilicate glass, borosilicate glass, crystal quartz, fused silica, synthetic silica, alumina silicate, silica, glass-ceramics or a mixture thereof. Among these materials, alumina, zirconia and silica are preferable as a main component in view of hardness.

<Particle Shapes>

In the present invention, inorganic fillers may be a population of indefinite-shape particles and a population of spherical-shape particles.

In the present invention, a filler of indefinite-shape particles is dispersed in an opaque layer to improve a light scattering property of the opaque layer. The improved property of the light scattering contributes to a concealment of metal color of dental metal bases. In the opaque layer containing the dispersed indefinite-shape particles, the incident light is irregularly reflected by the surface of respective dispersed particles. That is to say, the light transmission decreases through the opaque layer and the effect to conceal a metal color of dental metal frames is improved.

In the present invention, a filler of spherical-shape particles is dispersed in an opaque layer to improve a light transmission property (regular transmission) of the opaque layer. The improved property of the light transmission contributes to a color tone reproduction comparable with natural dental crowns. In the opaque layer containing the dispersed spherical-shape particles, the incident light is regularly reflected by the surface of respective dispersed particles. That is to say, the light transmission increases through the opaque layer and the effect of reproducing a color tone reproduction is improved.

In the present invention, shapes of filler particles are defined as the degrees of circularity of the particles, which are determined on the basis of the projected areas of particles and the boundary lengths of particles. The projected areas and the boundary lengths are obtained by taking an image of the particles with a scanning electron microscope (hereinafter called "SEM") and analyzing the image with an image analyzer.

Degrees of circularity of the particles are calculated from the following equation, where S is a projected area of a particle on an image and L is a boundary length of a particle:

$$\text{Degree of circularity of particle} = (4 \ast \pi \ast S)/(L^2).\qquad \text{[Equation 1]}$$

The number of particles to be analyzed per sample is 100 or more in average in order to obtain a reproducible constant value.

In the present invention, when a population of observed particles is round in shape and has a degree of circularity of 0.8 or more, the population of particle is referred to a filler of spherical-shape particles. When a population of observed particles has a degree of circularity of less than 0.8, the population of the particles is referred to a filler of indefinite-shape (non-spherical) particles.

The filler of indefinite-shape particles (a2) included in the first opaque material (A) preferably has a degree of circularity ranging from 0.4 to 0.7. The filler of spherical-shape particles (b2) included in the second opaque material (B) preferably has a degree of circularity equal to 0.8 or more.

<Particle Size>

An average particle size and a variation coefficient of particle sizes of filler may be obtained by analyzing a SEM image of the filler particles with an image analyzer, similar to the analysis of particle shapes.

The material strength of an opaque material in the cured form is influenced by average particle sizes of inorganic filler dispersed in the opaque material.

The average particle size of the indefinite-shape (non-spherical) inorganic filler (a2) included in the first opaque material (A) ranges from 0.1 μm to 20 μm. Preferably, the average particle size ranges from 1 μm to 10 μm. When an inorganic filler included in the opaque material has an average particle size of less than 0.1 μm, the opaque material in the cured form has a tendency to be weak. When the inorganic filler has an average particle size of more than 20 μm, the opaque material in the paste form has a tendency to exhibit inadequate operability.

The average particle size of the spherical-shape inorganic filler (b2) included in the second opaque material (B) ranges from 0.1 μm to 20 μm. Preferably, the average particle size ranges from 0.1 μm to 10 μm. When an inorganic filler included in the opaque material has an average particle size of less than 0.1 μm, the opaque material in the cured form may have a tendency to be weak because the filling rate of the polymerizable composition decreases. When the inorganic filler included in the opaque material has an average particle size of more than 20 μm, it is difficult to thinly and uniformly apply the pastes of the opaque material.

The inorganic filler (b2) of spherical-shape particles preferably comprises two kinds of fillers which have different average sizes of particles each other. In particular, the inorganic filler preferably comprises a population of small size particles and a population of large size particles of which an average particle size is larger than that of the small particles. The population of small size particles preferably has an average particle size ranging from 0.1 μm to 2.0 μm. The population of large size particles preferably has an average particle size ranging from 1.0 μm to 20 μm.

When an opaque material comprises two kinds of fillers having different average particle sizes each other, the opaque material is not stringy or sticky in the paste form unless an opaque material comprises only a population of small size particles. The opaque material comprising two kinds of fillers does not disconnect in applying the opaque material in the paste form unless an opaque material comprises only a population of large size particles.

By combining two kinds of fillers different in average particle size, the opaque material in the paste form has an adequate property and exhibits a good operability in use.

In the present invention, an average particle size is meant by a volume mean diameter. Volume mean diameter values are obtained from a particle size distribution measurement using a laser diffraction and scattering method suitable for measuring microparticles or by an analysis of an electron microscope image with a software for analyzing an image.

<Amount>

The inorganic filler (a2) of indefinite-shape particles included in an opaque material is in an amount ranging from 10 to 150 parts by weight, preferably from 20 to 140 parts by weight based on 100 parts of weight of the polymerizable monomer (a1). Preferably, the amount ranges from 25 to 125 parts by weight based on 100 parts of weight of the polymerizable monomer. When the amount is less than 10 parts by weight, the opaque material has a too low viscosity in the paste form. When the amount is more than 150 parts by weight, the opaque material has a too high viscosity in the paste form, resulting in an inadequate operability.

The inorganic filler (b2) of spherical-shape particles included in an opaque material is in an amount ranging from 10 to 200 parts by weight, preferably from 25 to 125 parts by weight based on 100 parts by weight of the polymerizable monomer (b1). Preferably, the amount ranges from 30 to 150 parts by weight based on 100 parts by weight of the polymerizable monomer. When the amount is less than 10 parts by weight, the opaque material has a too low viscosity in the paste form. When the amount is more than 200 parts by weight, the opaque material has a too high viscosity in the paste form, resulting in an inadequate operability.

<Refractive Index>

The inorganic fillers (a2) and (b2) have refractive index ranging from 1.4 to 1.6. When the inorganic fillers have a refractive index that is out of the range, the scattering effect increases because of a difference between the refractive index of the polymerizable monomer and that of the inorganic fillers. The inorganic fillers do not relatively affect the light permeability and light scattering effect of the opaque materials. As a result, the permeability and light scattering effect are not easily adjusted with the inorganic fillers included in the first and the second opaque layers, and it is difficult to yield a good color tone reproduction.

[Polymerization Catalyst]

Catalysts known in dental field may be used, without any limitation, for the polymerization catalysts (a3) and (b3). Examples of polymerization catalysts include benzophenone, diacetyl, benzyl, 4,4'-dimethoxybenzyl, 4,4'-dimethoxybenzyl, 4,4'-oxybenzyl, 4,4'-benzyl chloride, camphorquinone, camphorquinone carboxylic acid, 2,3-pentadione, 2,3-octadione, 9,10-phenanthrenequinone, acenaphthenequinone, 2,4,6-trimethylbenzoyl diphenylphosphineoxide, 2,6-dimethylbenzoyl diphenylphosphineoxide, 2,6-dimethoxybenzoyl diphenylphosphineoxide, 2,6-dichlorobenzoyl diphenylphosphineoxide, 2,3,5,6-tetramethylbenzoyl diphenylphosphineoxide, 2,4,6-trimethylbenzoylphenyl phosphinic methyl, 2,4,6-trimethylbenzoylphenyl phosphinic ethylester, and 2,4,6-trimethylbenzoylphenyl phosphinic phenylester. Examples of useful chemical polymerizable catalysts include diacyl peroxides, peroxyl esters, dialkyl peroxides, peroxy ketals, ketone peroxides, hydroperoxides. In particular, examples of diacy peroxides include benzoyl peroxide, 2,4-dichlorobenzoyl peroxide, and m-toluoyl peroxide.

Catalysts containing a tertiary amine are preferably used for the polymerization catalyst (a3) to increase adhesive strength. Tertiary amine compounds known in the dental field may be used, without any limitation, for the polymerization catalyst. Examples of the tertiary amine compounds include N,N-dimethyl aniline, N,N-diethyl aniline, N,N-dibenzyl aniline, N,N-dimethyl-p-toluidine, N,N-diethyl-p-toluidine, N,N-dihydroxyethyl-p-toluidine, N,N-dimethylbenzoic acid, N,N-diethylbenzoic acid, N,N-dimethyl benzoic acid ethyl, N,N-diethyl benzoic acid ethyl, N,N-dimethyl benzoic acid methyl, N,N-diethyl benzoic acid methyl, N,N-dimethylaminobenzaldehyde, N,N-dihydroxy ethylaniline, p-dimethylamino phenethyl alcohol, N,N-dimethylamino ethyl methacrylate, triethylamine, tributylamine, tripropylamine, and N-ethyl ethanolamine. Among of these compounds, aromatic tertiary amine compounds are preferably used. Preferably used are N,N-dimethyl benzoic acid ethyl, N,N-diethyl benzoic acid ethyl, N,N-dimethyl benzoic acid methyl, and N,N-dimethyl benzoic acid methyl.

[Obscure Material]

<Amount>

The first opaque material (A) is required to contain an obscure material (a4) to obscure a metal color of dental metal materials. The obscure material included in the first opaque material preferably is in an amount ranging from 0.5 to 20 parts by weight, further preferably from 1 to 15 parts by weight based on 100 parts of weight of the polymerizable monomer. When the amount is over the range, the mechanical strength of the opaque material may be inadequate in the cured form. When the amount is below the range, the concealment of the opaque material may be inadequate in the cured form.

The second opaque material (B) is required to contain an obscure material (b4) to obscure a metal color of dental metal materials. The obscure material included in the second opaque material preferably is in an amount ranging from 1 to 25 parts by weight, further preferably from 2 to 20 parts by weight based on 100 parts of weight of the polymerizable monomer. When the amount is over the range, the mechanical strength of the opaque material may be inadequate in the cured form. When the amount is below the range, the concealment of the opaque material may be inadequate in the cured form.

The obscure materials (a4) and (b4) are preferably so-called white pigment, particularly including an oxidation zirconia, an aluminum oxide, a magnesium oxide, a zinc oxide, a titanium oxide, barium sulfate, and a combination of at least two thereof. Further preferably, the obscure material is titanium oxide.

<Refractive Index>

The obscure material included in an opaque layer may conceal a metal color of dental metals by refracting the incident light at the opaque layer when the obscure material has a refractive index quite different from that of the polymerizable monomer. In the present invention, the concealing property of opaque layers may be adjusted by modifying an amount of the obscure materials. The difference between the index refractive of the obscure material and that of the polymerizable monomer is preferably more than 0.075, further preferably more than 0.1.

[Additional Agent]

(1) Microparticles

The opaque materials (A) and (B) may comprise a filler of microparticles of which an average particle size ranges from 1 nm to 100 nm to finely adjust the preservation stability and the operability. The opaque materials preferably comprises the filler of microparticles in amount ranging 0.01 to 20 parts by weight based on 100 parts of weight of the polymerizable monomer (a1) or (b1). When the amount is over 20 parts by weight, the operability of the opaque material may be inadequate in the paste form and the mechanical strength may be inadequate in the cured form.

(2) Pigment

The opaque materials (A) and (B) may comprise known organic or inorganic pigments such as black iron oxide pigments and yellow iron oxide pigments to aesthetically reproduce a natural dental crown color. An amount of pigment added to an opaque material may be visually checked. The amount of pigment is in such a range that the pigment does not substantially affect the colors of natural dental crowns when the second opaque material (B) is applied and cured on the natural dental crowns. When a photo-polymerization initiator used for curing, the amount of pigment is further in such a range that a dental curing light can reach every corner and substantially cure a light cure resin. The amount of pigments to meet these conditions ranges from 0.001 to 10 parts by weight based on 100 parts of weight of the opaque material (A) or (B).

(3) Organic Filler

The opaque materials (A) and (B) both may comprise organic filler. The organic filler preferably is in such an amount that a mechanical strength, a property for applying, a stain-resistance property from the use of a metal instrument, an operability, and a reproduction of color tone of the opaque materials are not inadequately affected. The amount is preferably less than 25 parts by weight.

(4) Other Agents

In the present invention, photo-polymerizable dental composition may optionally comprise a polymerization-inhibitor, an ultraviolet absorber, and a solvent.

Polymerization-inhibitors may include hydroquinone, hydroquinone monomethyl ether, and butylated hydroxytoluene, and preferably is hydroquinone monomethyl ether and butylated hydroxytoluene.

Solvates may include water, ethanol, i-propanol, acetone, dimethyl sulfoxide, dimethylformamide, ethyl acetate, and butyl acetate.

[Surface Treatment]

The above inorganic filler of spherical-shape particles and of indefinite-shape particles can be applied on a surface treated with conventional surface treatments. Examples of surface treatments includes, without any limitation, silane compounds, such as vinyl trimethoxysilane, vinyl triethoxysilane, vinyl trichlorosilane, vinyl tri(β-methoxyethoxy)silane, γ-methacryloxypropyl trimethoxysilane, γ-glycidoxypropyl trimethoxysilane, γ-mercaptopropyl trimethoxysilane, and γ-aminopropyl triethoxysilane. The organic filler may be composite powders (composite filler) which are obtained by dispersing inorganic filler in polymer powders of aforementioned polymerizable monomers or the polymerizable monomers and curing the dispersion.

[Retention Beads]

Generally, retention beads are applied to a surface of metals for dental crown in order to prevent the cured form of an opaque material or a resin from being peeled off from the metal surface by the anchoring effects. Known beads may be used, without any limitation, as retention beads. Such retention beads may be plastic beads of spherical shape because it is not needed to adjust the direction of the beads in applying an opaque material containing the beads. The particle size of beads may preferably range from 0.15 mm to 0.20 mm in view of retention of an opaque layer.

[Property of Opaque Material]

<Contrast Ratio>

The first opaque material (A) preferably has a contrast ratio ranging from 0.50 to 0.95 at a thick plate of 0.1 mm. When the contrast ratio is less than 0.5, a color of dental metals may affect the appearance of the upper construction. When more than 0.95, it is difficult to confirm the depth of applied layer of the first opaque material.

The second opaque material (B) preferably has a contrast ratio ranging from 0.70 to 0.99 at a thick plate of 0.1 mm. When the contrast ratio is less than 0.7, a color of the lower layer may affect the appearance of the upper construction.

<Pressurized Flow>

The opaque materials (A) and (B) are mainly operated in the paste form with a brush. A pressurized flow is used as an index of operability with a brush. The pressurized flow is calculated based on diameters of the spread of the paste under a certain pressure and in a certain time. A diameter of the spread opaque material is measured and an additional diameter which crosses the measured diameter is further measured. The pressurized flow is an average of the diameters. An opaque material has a high pressurized flow value when the opaque material easily flows under a certain pressure.

An opaque material with a low pressurized flow value does not easily droop under a certain pressure, and such opaque material is inadequate in view of operability. On the other hand, an opaque material with a high pressurized flow value easily droops, and such opaque material is inadequate because it is difficult for the opaque material to stay on the place where the opaque material is applied.

Therefore, the first opaque material (A) preferably has a pressurized flow ranging from 30 mm to 55 mm, further preferably from 38 mm to 50 mm; and the second opaque material (B) preferably has a pressurized flow ranging from 25 mm to 45 mm, further preferably from 28 mm to 37 mm.

Facing crowns are needed to have an adequate aesthetic view similar to natural dental crowns and therefore, a body and an enamel layer are conventionally formed by laminating a hard resin having a good aesthetic view on an opaque layer after forming an adequate opaque layer.

In the present invention, an upper construction is rebuilt-up. When the rebuilding-up described above is taken into account, the thickness of the first opaque material (A) and the second opaque material (B) preferably ranges from 0.1 mm to 0.5 mm, further preferably from 0.2 mm to 0.4 mm. In particular, the first opaque material preferably has a thickness ranging from 0.05 mm to 0.25 mm, further preferably from 0.1 mm to 0.2 mm. The second opaque material preferably has a thickness ranging from 0.025 mm to 0.25 mm, further preferably from 0.05 mm to 0.2 mm.

A twice or more applications of the second opaque material is preferable to provide a natural color tone as compared to one application to bring a color from the lower layer into invisible. In addition, the twice or more applications is preferable because it is easy to adjust the thickness of the layer of applied material. The thickness per a layer of applied material preferably ranges from 0.025 mm to 0.125 mm.

A further adhesion effect is expected by applying a metal surface treatment agent for adhesion (C) in addition to the opaque materials (A) and (B). The metal surface treatment agent preferably comprises volatile organic compounds, phosphoric acid and/or phosphonic acid-containing monomer.

A metal surface treatment agent for adhesion (C) is applied on a metal surface and dried. On the dried layer, the first opaque material (A) is applied and cured by photopolymerization and/or thermal polymerization. Then, the second opaque material (B) is applied and cured by photopolymerization and/or thermal polymerization preferably at least one or more.

<Operability>

When the opaque layer applied on a metal facing crown is not constant in thickness, it is difficult to reproduce uniform color tone. When the opaque material is stressed in the cured form, the stress is not uniformly distributed, possibly resulting in a decreased adhesion strength and impact resistance. Therefore, the opaque material is needed to have such a good operability that the opaque material is easily applied with a brush, is not stringy, and is uniformly applied on a metal facing crown.

When an opaque material to be applied on metal facing crowns has a high viscosity, i.e., flow property, the opaque material is not easily applied with a brush, is not stringy, and is not uniformly applied. On the other hand, when an opaque material has low viscosity, the opaque material is not uniformly applied because the opaque material easily droops from the place to which the opaque material is applied. Indeed, the applied opaque material has a different thickness on the edge of the dental metal where a layer of the opaque material tends to be thick. Further, when retention beads are applied on a metal facing crown, the first opaque material (A) is required to have a better operability as compared to the case that retention beads are not applied.

Therefore, the first opaque material (A) is required to have an adequate viscosity and operability so that the opaque material fully fill voids between retention beads and a layer can be formed with a sufficient thickness in order that the retention beads are fully buried. The second opaque material (B) is required to have a property so that the opaque material is thinly and uniformly applied on the cured form of the first opaque layer.

EXAMPLE

Hereinafter, the dental material set for obscuring a metal color is illustrated with reference to embodiments. Table 1 shows compositions of the embodiments of the first opaque material (A). Table 2 shows compositions of the embodiments of the second opaque material (B). Table 3 shows results of each property test. It should be understood that the detailed description and specific examples are not intended to limit the scope of the present invention.

The compounds used for the opaque materials (A) and (B) are described below. The following compounds are not intended to limit the scope of the present invention.

Bis-GMA: 2,2-bis(4-(2-hydroxy-3-methacryloyloxy-propoxy)phenyl)propane

UDMA: 1,6-bis(methacryloxy-2-ethyloxycarbonylamino)2,2,4-trimethylhexane

3G: Triethylene glycol dimethacrylate

NPG: Neopentyl glycol dimethacrylate

TMP: Trimethylolpropane

HEMA: 2-hydroxyethyl methacrylate

Aerosil (average particle size: 14 nm)

Organic-inorganic composite filler (average particle size: 10 μm)

CQ: camphorquinone

DM-3B: dimethylamino ethyl methacrylate

DMBE: dimethylamino-benzoic acid ethyl

Opaque material: Titanium oxide

Primer for bonding metal (Metal Link, available from Shofu, INC)

The average particle sizes, the degrees of circularity, and the compositions of the filler of indefinite-shape particles used in the Examples are shown below. The following filler are not intended to limit the scope of the present invention.

F-a1: average particle size: 3 μm, degree of circularity: 0.65, silica

F-a2: average particle size: 7 μm, degree of circularity: 0.64, silica

F-a3: average particle size: 40 μm, degree of circularity: 0.61, silica

F-a4: average particle size: 0.1 μm, degree of circularity: 0.75, alumina

F-a5: average particle size: 2 μm, degree of circularity: 0.60, alumina

F-a6: average particle size: 6 μm, degree of circularity: 0.61, alumina

F-a7: average particle size: 10 μm, degree of circularity: 0.65, barium glass

F-a8: average particle size: 20 μm, degree of circularity: 0.65, silica

The average particle sizes, the degrees of circularity, and the compositions of the filler of spherical-shape particles used in the Examples are shown below. The following filler are not intended to limit the scope of the present invention.

F-s1: average particle size: 40 μm, degree of circularity: 0.94, silica

F-s2: average particle size: 1 μm, degree of circularity: 0.93, silica

F-s3: average particle size: 3 μm, degree of circularity: 0.90, silica

F-s4: average particle size: 5 μm, degree of circularity: 0.88, silica-zirconia

F-s5: average particle size: 2 μm, degree of circularity: 0.84, silica-zirconia

F-s6: average particle size: 5 μm, degree of circularity: 0.82, silica

F-s7: average particle size: 3 μm, degree of circularity 0.81, silica-zirconia

F-s8: average particle size: 1 μm, degree of circularity: 0.94, silica

F-s9: average particle size: 0.7 μm, degree of circularity: 0.93, silica

F-s10: average particle size: 0.4 μm, degree of circularity: 0.95, silica

F-s11: average particle size: 0.1 μm, degree of circularity: 0.96, silica

F-a12: average particle size: 20 μm, degree of circularity: 0.90, silica

[Evaluation of Property]

<Average Particle Sizes of Particles, Variation Coefficients of Particle Sizes, and Degrees of Circularity>

Shapes of filler particles were determined by analyzing an image of the filler particles taken with a scanning electron microscope (hereinafter called "SEM"). The average particle sizes of particles, the variation coefficients of particle sizes, and the degrees of circularity were obtained by analyzing the SEM images with an imaging analyzer. The number of sample particles to be analyzed is more than 100. Here, the degrees of circularity of particles are determined by analyzing SEM images with an image analyzer. The degrees of circularity of particles are calculated from the equation: Degree of circularity of particle=$(4*\pi*S)/(L^2)$, where S is a projected area of particle on an SEM image and L is a boundary length of particle. The particle sizes are obtained from the equation: Equivalent circle diameter= $(4*S/\pi)^{1/2}$.

<Pressurized Flow>

An opaque materials 0.20 g is placed on a surface of a flat plate glass. A new flat plate glass is put on the opaque material so that the opaque material is sandwiched. A load is applied to the opaque material through the glasses for one minute. The weight of the upper flat plate glass is taken into account and the load is adjusted to amount to 400 gram-weight. For example, when a weight of the upper flat plate glass is 15 gram-weight, a load is applied to the upper glass at 385 gram-weight.

A diameter of the spread opaque material is measured and an additional diameter which crosses the measured diameter is measured. The average of the two diameters is defined as a pressurized flow (n=2).

Pressurized flow of the first opaque material (A): preferable range from 30 mm to 55 mm, further preferable range from 38 mm to 50 mm; and Pressurized flow of the second opaque material (B): preferable range from 25 mm to 45 mm, further preferable range from 28 mm to 37 mm.

<Color Tone Reproduction Test>

(i) Color Tone Reproduction of Opaque Materials

Metal facing crowns, to which retention beads are applied, are prepared according to conventional methods. After a primer for dental metals is applied to a metal and air dried, the first opaque material (A) is applied on the surface of the metal with a thickness of 0.1 mm and cured by photo-polymerization and/or thermo-polymerization.

Then, the second opaque material (B) is applied with a thickness of 0.05 mm and cured by photo-polymerization and/or thermo-polymerization. The procedure of applying and curing the second opaque material (B) is carried out twice. The surface is visually checked. When the opaque material in the cured form exhibits uniformity in color tone, the opaque material is evaluated as ○. When the opaque material in the cured form exhibits ununiformity in color tone due to optical reflection, the opaque material is evaluated as x.

(ii) Reproduction of Color Tone after Rebuilding-Up Hard Resin

An upper construction is conventionally rebuilt-up with a photo-polymerizable hard resin for dental crown (Solidex Body, Solidex Incisal, available from Shofu INC.) with a thickness of 0.8 mm. When the opaque material in the cured form exhibits uniformity in color tone of the body, the opaque material is evaluated as ○. When the opaque material in the cured form exhibits ununiformity in color tone of the body depending on angles, the opaque material is evaluated as x.

<Rubbing Test with Metal Instrument>

The second opaque material (B) is applied on a metal plate and cured by photo-polymerization and/or thermo-polymerization. Then, the opaque material is rubbed in the cured form with a metal instrument. When the surface of the opaque material is stained to be black, the opaque material is evaluated as x. When the surface of the opaque material is not stained, the opaque material is evaluated as ○.

<Adhesion Test>

A Gold-silver-palladium alloy (Gold 12%) for dental molding (Castwell M.C. available from GC Co., Ltd) is used as a test object which has a size of 20×20×t2 mm and to which retention beads are not applied. The surface of the test object is treated with waterproof abrasive papers #600 Grit and then, is treated by sandblasting. A primer for bonding metal (Metal Link, available from Shofu INC.) is applied on the sandblasted surface and air dried.

The first opaque material (A) is applied on the primer-treated surface and cured by photo-polymerization to form a first opaque layer.

The second opaque material (B) is applied on the first opaque layer and cured by photo-polymerization. The procedure of applying and curing is conducted twice to form a second opaque layer.

A photo-polymerizable hard resin for dental crown (Solidex Incisal 59, available from Shofu INC.) is rebuilt-up on the second opaque layer and cured by photo-polymerization in order to give an aesthetic view.

The photo-polymerization is carried out for tree minutes with a halogen curing light (Solidilite, available from Shofu INC.).

According to the above procedures, test samples are prepared and are applied to a heat cycle which comprises a step of immersing the test sample in a water at 4° C. for one minute and immersing it in a water at 60° C. for one minute. The cycle is repeated 2000 times. After the cycles, the adhesion strength between the surface of the test object and the surface of the first opaque material is measured with an instron at the loading rate of 1 mm/min.

<Contrast Ratio>

Contrast ratio is a measure of representing a transparency. A contrast ratio is calculated from Y value of XYZ color system which is defined in JIS Z8701. Among the tristimulus values, Y relates to brightness.

In particular, the opaque materials (A) and (B) are cured to form columns with a thickness of 0.1 mm. The cured forms are placed on a black or white background.

The C illuminant (color temperature 6774 K) defined as a standard illuminant in Commission Internationale de l'Eclairage (CIE) is irradiated and the Y vale of the reflected light is measured with a color measurement (KONICA MINOLTA Spectrophotometer CM-2002).

When the background is black, the Y is referred to Yb. When the background is white, the Y is referred to Yw. The contrast ratio (C) is obtained from Yb/Yw in the following equation. When the C value is close to 1, the cured forms are opaqueness. When the C value is close to zero, the cured forms are transparency.

$$\text{Contrast ratio }(c)=Yb/Yw, \quad \text{[Equation 2]}$$

where Yb is a Y value at black background, and Yw is a Y value at white background.

<Operability>

(A) First opaque material

○: When the first opaque material in the paste form is applied on a surface of a metal facing crown with a brush, the opaque material forms a thick layer and does not droop. When the opaque material is applied on a surface of a metal facing crown to which retention beads are applied, several voids between retention beads are fully filled with the opaque material.

Δ: When the first opaque material is applied in the paste form with a brush, although the operation of applying is sometimes felt to be inadequate the opaque material is uniformly applied and does not droop. When the opaque material is applied on a surface to which retention beads are applied, several voids between retention beads are filled with the opaque material.

x: Because of a low viscosity, when a thick layer is formed from the first opaque material, the opaque material droops.

Because of a high viscosity, an operation of applying the first opaque material with a brush is inadequate, the opaque material is stringy, and it is difficult to uniformly apply. When the opaque material is applied on a surface to which retention beads are applied, several voids between retention beads are not fully filled with the opaque material.

(B) Second Opaque Material

○: When the second opaque material in the paste form is applied on a surface of the cured form of the first opaque material with a brush, the second opaque material may be uniformly applied.

Δ: When the second opaque material is applied in the paste form with a brush, the second opaque material may be uniformly applied.

x: Because of a low viscosity, when a thick layer is formed from the second opaque material, the opaque material droops.

Because of a high viscosity, an operation of applying the second opaque material with a brush is inadequate, the opaque material is stringy, and it is difficult to uniformly apply.

TABLE 1

| Compositions of the first opaque materials (A) | | | | | | | | |
|---|---|---|---|---|---|---|---|---|
| Component | | A-1 | A-2 | A-3 | A-4 | A-5 | A-6 | A-7 |
| Filler of indefinite-shape particles | F-a1 | 20 | 70 | 20 | | 10 | | |
| | F-a2: | 40 | | | 50 | | | |
| | F-a3: | | | | | | | |
| | F-a4: | | | 20 | | 10 | | |
| | F-a5: | | | | 20 | | | |
| | F-a6: | | | | 30 | | | |
| | F-a7: | | | 40 | | 40 | | |
| | F-a8: | | | | | | | |

TABLE 1-continued

| Compositions of the first opaque materials (A) | | | | | | | | |
|---|---|---|---|---|---|---|---|---|
| Filler of spherical-shape particles | F-s1:<br>F-s2:<br>F-s3:<br>F-s4:<br>F-s6:<br>F-s5:<br>F-s7:<br>F-s8:<br>F-s9:<br>F-s11: | | | | | | 40<br><br><br>40 | <br><br><br><br>30<br><br><br>20<br>20 |
| Microparticles | Aerosil | 10 | 20 | 10 | 20 | 10 | 5 | 10 |
| Organic filler | | | | 5 | | | | 5 |
| Polymerizable monomer | Bis-GMA<br>UDMA<br>3 G<br>NPG<br>TMP<br>HEMA | 60<br><br>40 | <br>70<br>30 | 60<br><br><br>40 | <br>60<br><br><br>40 | <br>70<br>30 | 60<br><br>40 | 60<br><br><br>40 |
| Polymerization catalyst | CQ<br>DM-3B<br>DMBE | 0.5<br>0.3 | 0.4<br><br>0.5 | 0.3<br><br>1.0 | 0.2<br><br>0.3 | 0.4<br><br>0.5 | 0.5<br>0.3 | 0.3<br><br>1.0 |
| Obscure material | Titanium oxide | 1 | 3 | 5 | 7 | 5 | 4 | 6 |
| Pigment | | moderate amount | moderate amount | moderate amount | moderate amount | moderate amount | moderate amount | moderate amount |

| Component | | A-8 | A-9 | A-10 | A-11 | A-12 | A-13 | A-14 |
|---|---|---|---|---|---|---|---|---|
| Filler of indefinite-shape particles | F-a1<br>F-a2:<br>F-a3:<br>F-a4:<br>F-a5:<br>F-a6:<br>F-a7:<br>F-a8: | 20 | | <br><br>50 | <br><br><br><br><br><br><br>60 | 10 | 60<br>90 | 60<br>120 |
| Filler of spherical-shape particles | F-s1:<br>F-s2:<br>F-s3:<br>F-s4:<br>F-s6:<br>F-s5:<br>F-s7:<br>F-s8:<br>F-s9:<br>F-s11: | <br><br><br><br><br><br><br><br><br>10 | 50<br><br><br><br><br>20<br><br>20 | | | | | |
| Microparticles | Aerosil | 5 | 10 | 10 | 10 | 20 | 10 | 10 |
| Organic filler | | | | | | | | |
| Polymerizable monomer | Bis-GMA<br>UDMA<br>3 G<br>NPG<br>TMP<br>HEMA | <br>60<br><br><br>40 | 60<br><br>40 | <br>70<br>30 | 60<br><br>40 | <br>70<br>30 | 60<br><br>40 | 60<br><br>40 |
| Polymerization catalyst | CQ<br>DM-3B<br>DMBE | 0.2<br><br>0.3 | 0.5<br>0.3 | 0.4 | 0.5<br>0.3 | 0.4<br><br>0.5 | 0.5<br>0.3 | 0.5<br>0.3 |
| Obscure material | Titanium oxide | 7 | 5 | 5 | 1 | 3 | 1 | 1 |
| Pigment | | moderate amount | moderate amount | moderate amount | moderate amount | moderate amount | moderate amount | moderate amount |

TABLE 2

| Compositions of the second opaque materials (B) | | | | | | | | |
|---|---|---|---|---|---|---|---|---|
| Component | | B-1 | B-2 | B-3 | B-4 | B-5 | B-6 | B-7 |
| Filler of indefinite-shape particles | F-a1:<br>F-a2:<br>F-a4:<br>F-a5:<br>F-a6:<br>F-a7: | | | | | <br><br>20<br>20<br>30<br>10 | 40<br>40 | |

TABLE 2-continued

Compositions of the second opaque materials (B)

|  |  | B-1 | B-2 | B-3 | B-4 | B-5 | B-6 | B-7 |
|---|---|---|---|---|---|---|---|---|
| Filler of spherical-shape particles | F-s1: |  |  |  |  |  |  |  |
|  | F-s2: | 40 |  |  |  |  |  |  |
|  | F-s3: |  | 20 |  |  |  |  |  |
|  | F-s4: |  |  |  | 20 |  |  |  |
|  | F-s6: |  | 40 | 40 |  |  |  |  |
|  | F-s5: |  |  | 40 | 20 |  |  | 40 |
|  | F-s7: | 20 |  |  | 20 |  |  |  |
|  | F-s8: |  | 20 |  |  |  |  |  |
|  | F-s9: |  |  | 20 |  | 20 |  | 40 |
|  | F-s11: | 10 |  |  | 20 |  |  |  |
|  | F-s12: |  |  |  |  |  |  |  |
| Microparticles | Aerosil | 8 | 4 | 4 | 8 | 4 | 8 | 8 |
| Organic filler |  |  | 15 | 10 | 5 | 15 |  | 10 |
| Polymerizable monomer | Bis-GMA | 40 | 30 | 40 |  | 30 | 40 | 40 |
|  | UDMA | 40 | 30 | 20 | 70 | 30 | 40 | 20 |
|  | 3 G |  | 20 | 10 | 30 | 20 |  | 10 |
|  | NPG |  |  | 10 |  |  |  | 10 |
|  | TMP |  | 20 | 10 |  | 20 |  | 10 |
|  | HEMA | 20 |  | 10 |  |  | 20 | 10 |
| Polymerization catalyst | CQ | 0.5 | 1 | 2 | 4 | 1 | 0.5 | 2 |
|  | DM-3B | 0.2 | 1 | 2 | 1 | 1 | 0.2 | 2 |
|  | DMBE | 0.2 |  |  | 1 |  | 0.2 |  |
| Obscure material | Titanium oxide | 7 | 10 | 12 | 15 | 10 | 7 | 12 |
| Pigment |  | moderate amount | moderate amount | moderate amount | moderate amount | moderate amount | moderate amount | moderate amount |

|  |  | B-8 | B-9 | B-10 | B-11 | B-12 | B-13 | B-14 |
|---|---|---|---|---|---|---|---|---|
| Filler of indefinite-shape particles | F-a1: |  |  |  |  |  |  |  |
|  | F-a2: | 20 |  |  |  |  |  |  |
|  | F-a4: |  |  |  |  |  |  |  |
|  | F-a5: | 10 |  |  |  |  |  |  |
|  | F-a6: | 20 |  |  |  |  |  |  |
|  | F-a7: |  |  |  |  |  |  |  |
| Filler of spherical-shape particles | F-s1: |  |  |  |  |  |  | 40 |
|  | F-s2: | 20 |  |  |  | 10 |  |  |
|  | F-s3: |  |  |  |  |  | 40 |  |
|  | F-s4: |  |  |  |  |  |  |  |
|  | F-s6: | 20 |  |  |  |  | 20 |  |
|  | F-s5: |  |  |  |  |  |  |  |
|  | F-s7: |  | 10 | 220 |  |  |  | 20 |
|  | F-s8: |  |  |  |  |  | 90 |  |
|  | F-s9: |  |  |  |  |  |  |  |
|  | F-s11: |  |  |  |  |  |  | 10 |
|  | F-s12: |  |  |  | 70 |  |  |  |
| Microparticles | Aerosil | 4 | 6 | 6 | 8 | 8 | 4 | 8 |
| Organic filler |  | 5 |  |  |  |  | 15 |  |
| Polymerizable monomer | Bis-GMA |  | 40 | 30 | 40 | 40 | 30 | 40 |
|  | UDMA | 70 | 40 | 30 | 40 | 40 | 30 | 40 |
|  | 3 G | 30 |  | 20 |  |  | 20 |  |
|  | NPG |  |  |  |  |  |  |  |
|  | TMP |  |  | 20 |  |  | 20 |  |
|  | HEMA |  | 20 |  | 20 | 20 |  | 20 |
| Polymerization catalyst | CQ | 4 | 0.5 | 1 | 0.5 | 0.5 | 1 | 0.5 |
|  | DM-3B | 1 | 0.2 | 1 | 0.2 | 0.2 | 1 | 0.2 |
|  | DMBE | 1 | 0.2 |  | 0.2 | 0.2 |  | 0.2 |
| Obscure material | Titanium oxide | 15 | 10 | 10 | 7 | 7 | 10 | 7 |
| Pigment |  | moderate amount | moderate amount | moderate amount | moderate amount | moderate amount | moderate amount | moderate amount |

TABLE 3

|  | Example 1 | Example 2 | Example 3 | Example 4 | Example 5 | Example 6 | Example 7 | Example 8 | Example 9 | Example 10 |
|---|---|---|---|---|---|---|---|---|---|---|
| First opaque materials (A) | A-1 | A-2 | A-3 | A-4 | A-11 | A-12 | A-13 | A-1 | A-1 | A-1 |
| Second opaque materials (B) | B-1 | B-2 | B-3 | B-4 | B-1 | B-1 | B-1 | B-11 | B-12 | B-13 |
| Contrast ratio | 0.60 | 0.70 | 0.77 | 0.80 | 0.58 | 0.67 | 0.63 | 0.60 | 0.60 | 0.60 |
| Upper layer: A Lower layer: B | 0.96 | 0.97 | 0.97 | 0.99 | 0.96 | 0.96 | 0.96 | 0.96 | 0.91 | 0.97 |

TABLE 3-continued

| | | | | | | | | | | |
|---|---|---|---|---|---|---|---|---|---|---|
| Pressurized flow Upper layer: A | 49.6 | 47.8 | 32.7 | 30.0 | 34.1 | 49.5 | 30.5 | 49.6 | 49.6 | 49.6 |
| Lower layer: B | 36.4 | 29.9 | 38.0 | 32.8 | 36.4 | 36.4 | 36.4 | 39.2 | 43.0 | 25.6 |
| Adhesive strenght [MPa] | 25 | 28 | 23 | 22 | 26 | 20 | 24 | 25 | 26 | 25 |
| Color tone reproduction (1) Color tone reproduction of opaque material | ○ | ○ | ○ | ○ | ○ | ○ | ○ | ○ | ○ | ○ |
| Color tone reproduction (2) Color tone reproduction after rebuilding-up hard resin | ○ | ○ | ○ | ○ | ○ | ○ | ○ | ○ | ○ | ○ |
| Metal stain | ○ | ○ | ○ | ○ | ○ | ○ | ○ | ○ | ○ | ○ |
| Operability | ○ | ○ | ○ | ○ | ○ | Δ | ○ | ○ | ○ | ○ |
| Upper layer: A Lower layer: B | ○ | ○ | ○ | ○ | ○ | ○ | ○ | Δ | ○ | ○ |

| | Comparative Example 1 | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|
| First opaque materials (A) | A-5 | A-6 | A-7 | A-8 | A-9 | A-10 | A-14 | A-1 |
| Second opaque materials (B) | B-5 | B-6 | B-7 | B-8 | B-9 | B-10 | B-1 | B-14 |
| Contrast ratio Upper layer: A | 0.83 | 0.80 | 0.81 | 0.82 | 0.70 | 0.75 | 0.72 | 0.60 |
| Lower layer: B | 0.98 | 0.96 | 0.97 | 0.99 | 0.99 | 0.99 | 0.96 | 0.96 |
| Pressurized flow Upper layer: A | 37.7 | 44.6 | 36.2 | 46.7 | 45.6 | 35.6 | 27.8 | 49.6 |
| Lower layer: B | 38.6 | 35.0 | 33.1 | 50.6 | 50.0 | 20.0 | 36.4 | 31.1 |
| Adhesive strenght [MPa] | 21 | 13 | 13 | 18 | 15 | 20 | 20 | 24 |
| Color tone reproduction (1) Color tone reproduction of opaque material | x | x | x | x | x | x | ○ | x |
| Color tone reproduction (2) Color tone reproduction after rebuilding-up hard resin | x | x | x | x | x | ○ | ○ | ○ |
| Metal stain | x | x | ○ | x | ○ | ○ | ○ | ○ |
| Operability | ○ | x | x | x | x | x | x | ○ |
| Upper layer: A Lower layer: B | x | x | ○ | x | x | x | ○ | x |

When a first opaque material (A) comprises a filler of spherical-shape particles, the opaque material has a tendency to decrease in mechanical strength and adhesive strength in the cured form, and to have a low viscosity in the paste form. The low viscosity is inadequate in view of operability. When a thick layer is formed from the paste, the paste has a tendency to droop. When a second opaque material (B) comprises a filler of indefinite-shape (non-spherical) particles, the opaque material has a tendency to be stained with a metal color because the metal instrument is shaved at edges of the indefinite-shape particles. In addition, when such second opaque material is used, it is difficult to uniformly apply and a good color tone reproduction comparable with natural dental crowns is not obtained.

When first (A) and second (B) opaque materials both comprise a filler of spherical-shape particles, the opaque materials have a low adhesive strength. In addition, when such first opaque material (A) is applied, a layer formed from the opaque material does not stay at the place and droops. When several voids between retention beads are not filled with such first opaque material (A), the opaque material is evaluated as inadequate operability. When the filler is spherical-shape particles, irregular refraction of light tends not to occur and light transmission may possibly occur. As a result, the second opaque layer does not completely reproduce opaque color and a good color tone reproduction comparable with natural dental crowns is not obtained.

When first (A) and second (B) opaque materials both comprise a filler of indefinite-shape particles, a metal stain which is caused by the use of metal instrument tends to be occurred on the surface of such second opaque material. The second opaque layer has an irregular surface, resulting in an inadequate color tone reproduction. Because of the irregular surface, irregular refraction of light occurs and a uniform color tone reproduction to be desired is not obtained.

Surprisingly, it could be found that a dental membrane which contains the first opaque layer containing a filler of indefinite-shape particles and the second opaque layer containing a filler of spherical-shape particles exhibits a uniform color tone of base materials which is a lower layer of the second opaque layer, resulting in a high-quality tone reproduction comparable with natural dental crowns.

A high effect for obscuring a metal color may be obtained by the use of indefinite-shape particles in the first opaque layer because of a high effect of light scattering in the first opaque layer. A high-quality tone reproduction comparable with natural dental crowns may obtained by the use of spherical-shape particles in the second opaque layer which is formed on the first opaque layer because of an adequate light permeability in the second opaque layer.

The present invention provides a dental material set for obscuring a metal color and a method of forming a membrane for obscuring a metal color. The opaque materials of the dental material set exhibit a good color tone reproduction comparable with natural dental crowns and an adequate physical strength for opaque materials for obscuring metal color as well as a durable adhesiveness in the cured form. In the paste form, the opaque materials have a good property that a user easily operates. The opaque materials exhibit a stain-resistance property in rebuilding-up a dental composition on the opaque materials in the cured form with a metal instrument. The opaque materials according to the present invention are used as opaque materials for obscuring a color of base, e.g., filler, bonding agents, surface coating materials, crown restoration materials, and cement.

EXPLANATION OF SIGNS

1 Metal surface
2 First opaque layer
21 Resin in the cured form
22 Inorganic filler of indefinite form
3 Second opaque layer
31 Resin in the cured form
32 Inorganic filler of spherical-shape particles
4 Surface treatment agent
5 Retention beads

What is claimed is:

1. A method of forming a two-layer membrane for obscuring a metal color, comprising the steps of:
    applying a first opaque material (A) on a dental metal surface and curing the first opaque material through photo-polymerization and/or thermo-polymerization to form a first opaque layer; and
    applying a second opaque material (B) on the first opaque layer at least one time or more, and curing the second opaque material through photo-polymerization and/or thermo-polymerization to form a second opaque layer,
    wherein the first opaque material (A) contains
a polymerizable monomer (a1) in an amount of 100 parts by weight;
an inorganic filler (a2) of indefinite-shape particles whose average particle size ranges from 0.1 µm to 20 µm in an amount ranging from 10 to 150 parts by weight;
a polymerization catalyst (a3) in an amount ranging from 0.1 to 10 parts by weight; and
an obscure material (a4) in an amount ranging from 0.5 to 20 parts by weight, and
    wherein the second opaque material contains
a polymerizable monomer (b1) in an amount of 100 parts by weight;
an inorganic filler (b2) of spherical-shape particles whose average particle size ranges from 0.1 µm to 20 µm in an amount ranging from 10 to 200 parts by weight;
a polymerization catalyst (b3) in an amount ranging from 0.5 to 20 parts by weight; and
an obscure material (b4) in an amount ranging from 1 to 25 parts by weight.

2. The method according to claim 1, comprising the step of:
    applying a metal surface treatment agent for adhesion (C) on the dental metal surface,
    wherein the first opaque layer is formed on the dental metal surface treated with the metal surface treatment agent for adhesion (C) after the metal surface treatment agent for adhesion (C) is dried.

3. The method according to claim 1, wherein the indefinite-shape particles of the inorganic filler (a2) have a degree of circularity of less than 0.8 and the spherical-shape particles of the inorganic filler (b2) have a degree of circularity of 0.8 or more.

4. The method according to claim 3, wherein the indefinite-shape particles of the inorganic filler (a2) have a degree of circularity ranging from 0.4 to 0.7.

5. The method according to claim 3, wherein the first opaque material (A) and the second opaque material (B) each further comprises a filler of fine particles whose average particle size ranges from 1 nm to 100 nm; and
    wherein the first opaque material (A) contains the filler of fine particles in an amount from 0.01 to 20 parts by weight based on 100 parts of weight of the polymerizable monomer (a1) and wherein the second opaque material (B) contains the filler of fine particles in an amount from 0.01 to 20 parts by weight based on 100 parts by weight of the polymerizable monomer (b1).

6. The method according to claim 3, wherein the first opaque material (A) and/or the second opaque material (B) further comprises a pigment.

7. The method according to claim 3, wherein the polymerization catalyst (a3) contains at least a tertiary amine compound.

8. The method according to claim 3, wherein the second opaque material (B) further comprises an organic-inorganic composite filler.

* * * * *